United States Patent
Tada et al.

(10) Patent No.: US 10,619,182 B2
(45) Date of Patent: Apr. 14, 2020

(54) METHOD, DEVICE AND SYSTEM FOR TESTING DRUG SENSITIVITY

(71) Applicant: HITACHI, LTD., Tokyo (JP)

(72) Inventors: Hiroko Tada, Tokyo (JP); Hideyuki Noda, Tokyo (JP); Hideki Niimi, Toyama (JP); Isao Kitajima, Toyama (JP)

(73) Assignee: Hitachi, Ltd., Tokyo (JP)

( * ) Notice: Subject to any disclaimer, the term of this patent is extended or adjusted under 35 U.S.C. 154(b) by 156 days.

(21) Appl. No.: 15/526,388

(22) PCT Filed: Dec. 26, 2014

(86) PCT No.: PCT/JP2014/084455
§ 371 (c)(1),
(2) Date: May 12, 2017

(87) PCT Pub. No.: WO2016/103433
PCT Pub. Date: Jun. 30, 2016

(65) Prior Publication Data
US 2017/0314057 A1    Nov. 2, 2017

(51) Int. Cl.
*C12Q 1/00*        (2006.01)
*C12Q 1/18*        (2006.01)
(Continued)

(52) U.S. Cl.
CPC ............ *C12Q 1/18* (2013.01); *C12M 1/34* (2013.01); *C12Q 1/008* (2013.01); *C12Q 1/66* (2013.01)

(58) Field of Classification Search
CPC ......... C12M 37/00; C12M 37/06; C12Q 1/66; C12Q 1/18; C12Q 1/34
See application file for complete search history.

(56) References Cited

U.S. PATENT DOCUMENTS

| 4,390,274 A | 6/1983 | Berthold et al. |
| 5,798,263 A | 8/1998 | Wood et al. |

(Continued)

FOREIGN PATENT DOCUMENTS

| JP | 08-304402 A | 11/1996 |
| JP | 2008-17723 A | 1/2008 |

(Continued)

OTHER PUBLICATIONS

Thore A. et al., "Effects of Ampicillin on Intracellular Levels of Adenosine Triphosphate in Bacterial Cultures Related to Antibiotic Susceptibility", Acta Path. Microbiol, Scand. Sect. B, 1977, vol. 85, pp. 161-166.

(Continued)

*Primary Examiner* — Nathan A Bowers
(74) *Attorney, Agent, or Firm* — Mattingly & Malur, PC (57) ABSTRACT

When bacteria growth is determined in the related art using an ATP method, the bacteria growth is determined, based on an increase or a decrease in live bacteria ATP with the lapse of a culture time. Accordingly, it is necessary to measure the live bacteria ATP multiple times while antimicrobial susceptibility culture is carried out. It takes time and labor in sample preparation for each measurement, and it is difficult to quickly obtain an antimicrobial susceptibility result. Therefore, according to the present invention, the presence or absence of antimicrobial susceptibility of bacteria is determined, based on an ATP luminescence amount derived from dead bacteria in a culture liquid.

20 Claims, 9 Drawing Sheets

(51) Int. Cl.
*C12M 1/34* (2006.01)
*C12Q 1/66* (2006.01)

(56) References Cited

U.S. PATENT DOCUMENTS

| | | | |
|---|---|---|---|
| 9,360,404 B2* | 6/2016 | Okanojo | B01L 3/5635 |
| 2011/0171684 A1* | 7/2011 | Yamamoto | C12Q 1/04 |
| | | | 435/39 |
| 2012/0149045 A1* | 6/2012 | Niles | C12Q 1/37 |
| | | | 435/8 |
| 2014/0342386 A1* | 11/2014 | Okanojo | C12Q 1/42 |
| | | | 435/18 |

FOREIGN PATENT DOCUMENTS

| | | | |
|---|---|---|---|
| JP | 2008-178420 A | | 8/2008 |
| JP | 2013116083 A | * | 6/2013 |
| WO | 2006/070752 A1 | | 7/2006 |

OTHER PUBLICATIONS

Nilson, "New Rapid Bioassay of Gentamicin Based on Luciferase Assay of Extracellular ATP in Bacterial Cultures", Antimicrobial Agents and Chemother, 1978, vol. 14, No. 6, pp. 812-816.
International Search Report of PCT/JP2014/084455 dated Feb. 17, 2015.
Japanese Office Action received in corresponding Japanese Application No. 2018-239184 dated Dec. 3, 2019.

* cited by examiner

(1) LIVE BACTERIA ATP

(2) SUBMERGED ATP (3) FILTRATE ATP (4) TOTAL ATP

[Fig. 3]

| | METHOD (1) LIVE BACTERIA ATP | METHOD (2) SUBMERGED ATP | METHOD (3) FILTRATE ATP | METHOD (4) TOTAL ATP |
|---|---|---|---|---|
| ATP INCLUDED IN CELL MEMBRANE OF LIVE BACTERIA (HAVING CELL MEMBRANE) | ○ | × | × | ○ |
| ATP INCLUDED IN CELL MEMBRANE OF DEAD BACTERIA (HAVING CELL MEMBRANE) | ○ | × | × | ○ |
| ATP INCLUDED IN CELL MEMBRANE OF DEAD BACTERIA (HAVING DAMAGED CELL MEMBRANE) | × | ○ | × | ○ |
| FREE ATP DERIVED FROM DEAD BACTERIA (HAVING DAMAGED CELL MEMBRANE) | × | ○ | ○ | ○ |

○: MEASUREMENT AVAILABLE  ×: MEASUREMENT UNAVAILABLE

| TYPE OF BACTERIA / LUMINESCENCE AMOUNT | x | y | x/y |
|---|---|---|---|
| BACTERIUM A | x1 | y1 | A |
| BACTERIUM B | x2 | y2 | B |

METHOD, DEVICE AND SYSTEM FOR TESTING DRUG SENSITIVITY

TECHNICAL FIELD

The present invention relates to a bacteria growth evaluation, and particularly relates to a method, a device, and a system for carrying out an antimicrobial susceptibility test of bacteria.

BACKGROUND ART

Since the number of deaths increases and antimicrobial-resistant bacteria appear due to an infectious disease, an antimicrobial susceptibility test of infectious disease-causing bacteria is noticeably expedited. In the related art, the antimicrobial susceptibility test has been carried out based on a culture method. After a specimen such as blood, pharyngeal swab, and sputum is collected from an infectious patient, isolation culture is carried out overnight in order to obtain the infectious disease-causing bacteria as a single colony from the specimen in which indigenous bacteria coexist. Furthermore, after the bacteria forming the single colony are prepared to have a constant concentration, the bacteria are distributed to a container in which various types and various concentrations of antimicrobials/antibiotics are arranged, and antimicrobial susceptibility culture is carried out overnight. Then, after the culture, a result of the antimicrobial susceptibility test of the infectious disease-causing bacteria is obtained, based on the presence or absence of bacterial growth. In accordance with the received result, a proper antimicrobial is administered to a patient. Therefore, the proper antimicrobial is administered to the infectious patient three days later after the specimen is collected.

In contrast, as a method of quickly carrying out the antimicrobial susceptibility test, an ATP (Adenosine Triphosphate) bioluminescence method is noticeably used in which a change amount of ATP existing as an energy source inside the bacteria functions as an indicator of the bacteria growth. The ATP method is used in detecting the ATP existing as the energy source inside the bacteria by using firefly-derived enzyme luciferase. The luciferase oxidizes luciferin which serves as a substrate in the presence of ATP and $Mg^{2+}$ inside the bacteria, and a luminescence amount generated at that time is proportional to an ATP amount. Accordingly, the bacteria growth can be evaluated, based on a change in the luminescence amount. For example, as a method of determining the number of bacteria by using the ATP method, PTL 1 discloses a technique in which the number of live bacteria and dead bacteria is obtained by counting the live bacteria through ATP measurement, counting total bacteria through a DNA method, and subtracting the live bacteria from the total bacteria.

CITATION LIST

Patent Literature

PTL 1: JP-A-08-304402

SUMMARY OF INVENTION

Technical Problem

When the bacteria growth is determined in the related art using the ATP method, free ATP is eliminated from the specimen so as to evaluate only ATP (live bacteria ATP) inside a bacterial cell which is alive. According to this method, the bacteria growth is determined, based on an increase or a decrease in the live bacteria ATP with the lapse of a culture time. Accordingly, it is necessary to measure the live bacteria ATP multiple times while antimicrobial susceptibility culture is carried out. Consequently, it takes time and labor in sample preparation for each measurement, and it is difficult to quickly obtain the antimicrobial susceptibility result.

Solution to Problem

In order to solve at least one problem in the above-described problems, according to an aspect of the present invention, there is provided an antimicrobial susceptibility test device including a measurement unit that measures ATP luminescence of a culture liquid containing an antimicrobial and bacteria, and a determination unit that determines the presence or absence of antimicrobial susceptibility of the bacteria, based on an ATP luminescence amount derived from dead bacteria in the culture liquid measured by the measurement unit.

Advantageous Effects of Invention

According to the present invention, an ATP antimicrobial susceptibility test is quickly and easily carried out, thereby enabling antibiotics to be promptly and properly administered to an infectious patient. An object, a configuration, and an advantageous effect in addition to those which are described above will be clarified by description of the following embodiment.

DESCRIPTION OF EMBODIMENTS

Hereinafter, a preferred form for embodying the present invention will be described with reference to the drawings and an embodiment. However, unless otherwise specifically described, a dimension, a material, a shape, and other relative arrangements of a system, an apparatus, a device, and a member are not intended to limit the scope of the present invention, and are just description examples.

Figure 1:
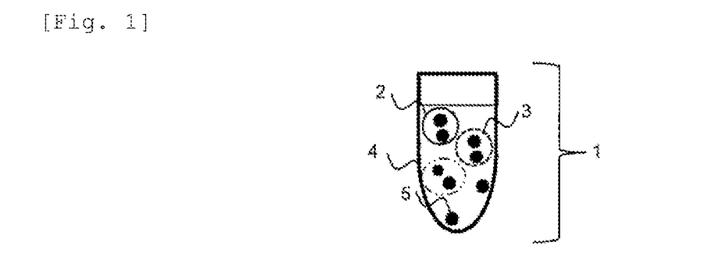
FIG. 1 is a view illustrating a configuration example of a bacteria culture liquid which serves as a target of an antimicrobial susceptibility test.

A bacteria culture liquid 1 serving as a target of an antimicrobial susceptibility test according to the present embodiment will be described with reference to FIG. 1. The bacteria culture liquid 1 contains bacteria existing in various states, such as a live bacterium 2, a dead bacterium 3 having no damage to a cell membrane, and a dead bacterium 4 having a damaged cell membrane. In the bacteria culture liquid 1, the live bacterium 2 and the dead bacterium 3 having no damage to the cell membrane include ATP inside the cell membrane. On the other hand, in the dead bacterium 4 having the damaged cell membrane, ATP leaks from a damaged portion of the cell membrane as the cell membrane is progressively damaged. Accordingly, ATP derived from the dead bacterium 4 having the damaged cell membrane exists as free ATP5 in the culture liquid.

Figure 2:
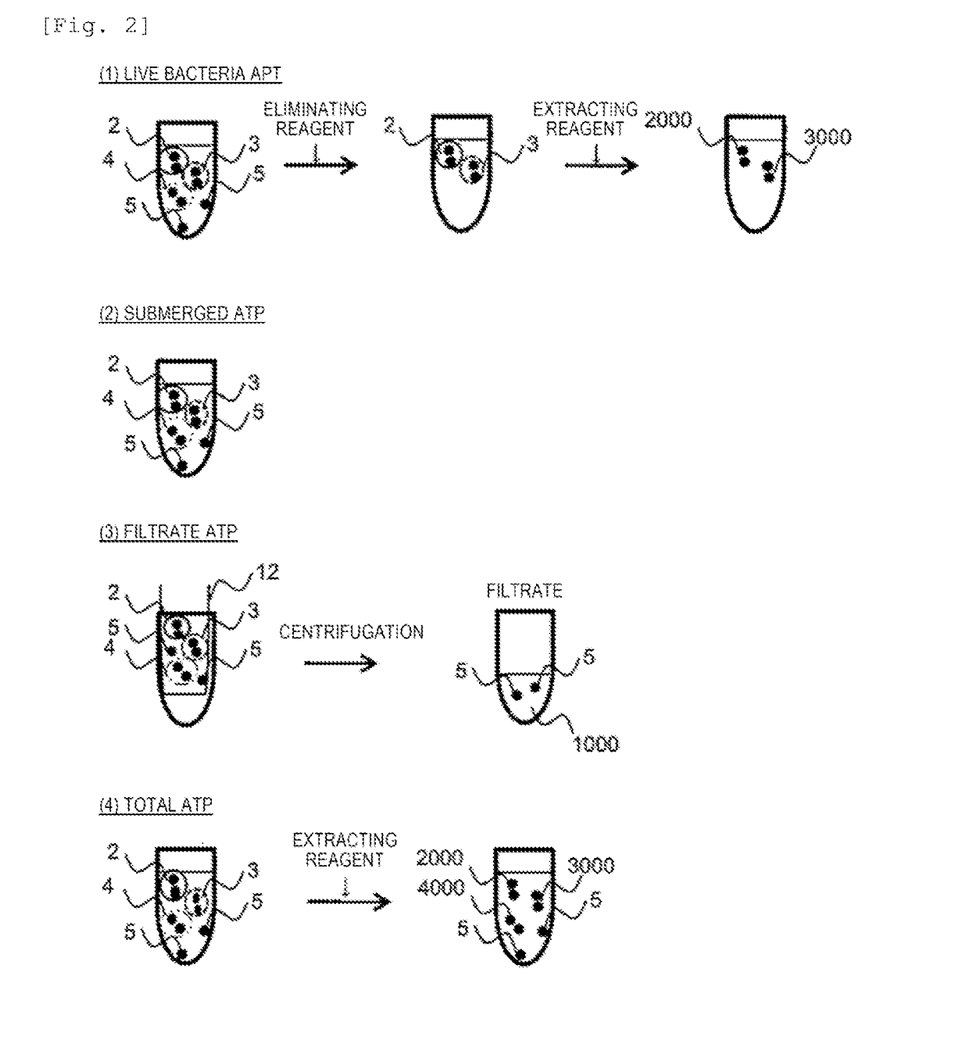
FIG. 2 is a view schematically illustrating a sample preparation method for measuring live bacteria ATP and dead bacteria ATP.

Next, a method for measuring ATP derived from the live bacteria and the dead bacteria will be described with reference to FIG. 2. A live bacteria ATP method in Method (1) is used in eliminating ATP5 outside a bacterial cell so as to measure ATP2000 included in the cell membrane of the live bacterium 2 and ATP3000 included in the cell membrane of the dead bacterium 3 having no damage to the cell membrane. A submerged ATP method in Method (2) is used in measuring the dead bacteria 4 having the damaged cell membrane and the free ATP5 in the culture liquid 1 while the bacterial cells of the live bacterium 2 and the dead bacteria 3 and 4 are included. The dead bacterium 4 serves as a measurement target, since a substrate and enzyme of enzyme luciferase reaction which are bioluminescent molecules (to be described later) enter the dead bacterium 4 from a damaged site. A filtrate ATP method in Method (3) is used in measuring the free ATP5 contained in a filtrate 1000 by removing bacterial cells 2, 3, and 4 in such a way that the culture liquid 1 is filtered through centrifugation using a filtering container 12 (to be described later). A total ATP method in Method (4) is used in extracting ATP2000 included in the cell membrane of the live bacterium 2, ATP3000 included in the cell membrane of the dead bacterium 3 having no damage to the cell membrane, and ATP4000 remaining inside the cell membrane of the dead bacterium 4 having the damaged cell membrane so as to measure all of these together with the free ATP5.

Figure 3:
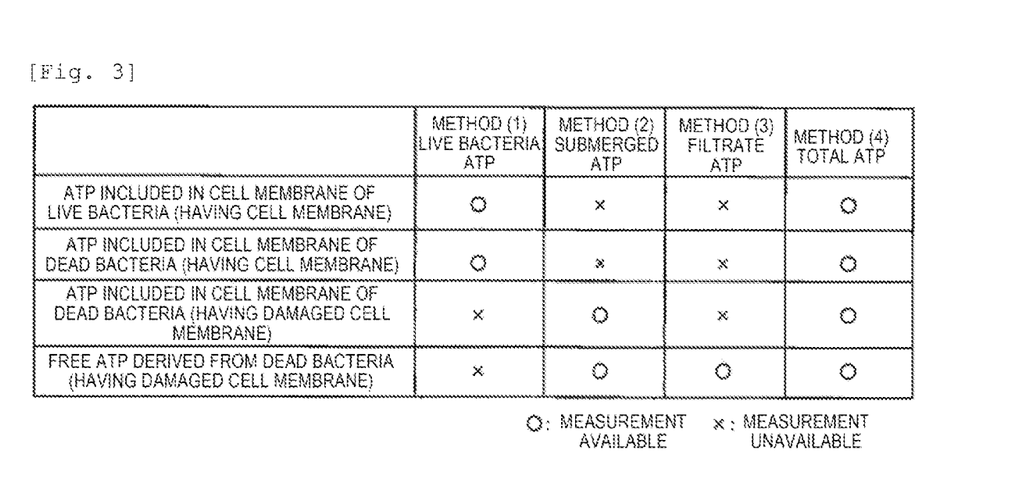
FIG. 3 is a table illustrating ATP which can be measured using each method.

ATP in the culture liquid 1 which can be measured using Methods (1) to (4) described above is illustrated in an organized manner in FIG. 3. According to method (1), it is possible to measure ATP included in the cell membrane of the live bacteria (having the cell membrane) and ATP included in the cell membrane of the dead bacteria (having the damaged cell membrane). According to Method (2), it is possible to measure ATP included in the cell membrane of the dead bacteria (having the damaged cell membrane) and the free ATP derived from the dead bacteria (having the damaged cell membrane). According to Method (3), it is possible to measure the free ATP derived from the dead bacteria (having the cell membrane). According to Method (4), it is possible to measure ATP included in the cell membrane of the live bacteria (having the cell membrane), ATP included in the cell membrane of the dead bacteria (having the cell membrane), ATP included in the cell membrane of the dead bacteria (having the damaged cell membrane), and the free ATP derived from the dead bacteria (having the damaged cell membrane).

In this way, ATP derived from the dead bacteria which exists in the culture liquid 1 as the free ATP5 is included in Methods (2) to (4). Accordingly, dead bacteria ATP can be measured using Methods (2) to (4), based on the amount of the free ATP5.

Next, a result example obtained in such a way that *E. coli* as an example is processed according to Methods (1) to (4) so as to measure an ATP amount will be described with reference to FIGS. 4a and 4b. The ATP method is a bioluminescence detection method of detecting ATP existing as an energy source in bacteria by using firefly-derived enzyme luciferase. The luciferase oxidizes luciferin which serves as a substrate in the presence of ATP and $Mg^{2+}$ inside the bacteria, and a luminescence amount generated at that time is proportional to the ATP amount. Accordingly, bacteria growth is evaluated, based on a change in the luminescence amount.

In the present embodiment, the luminescence amount is represented by integration of a photon count value of 60 sec, and the unit is defined as the luminescence amount (amount of luminescence (a.u.)). As described above, the luminescence amount and the ATP amount are in a proportional relationship. In a case where the luminescence amount increases, it is determined that the ATP amount increases.

Figure 4A:
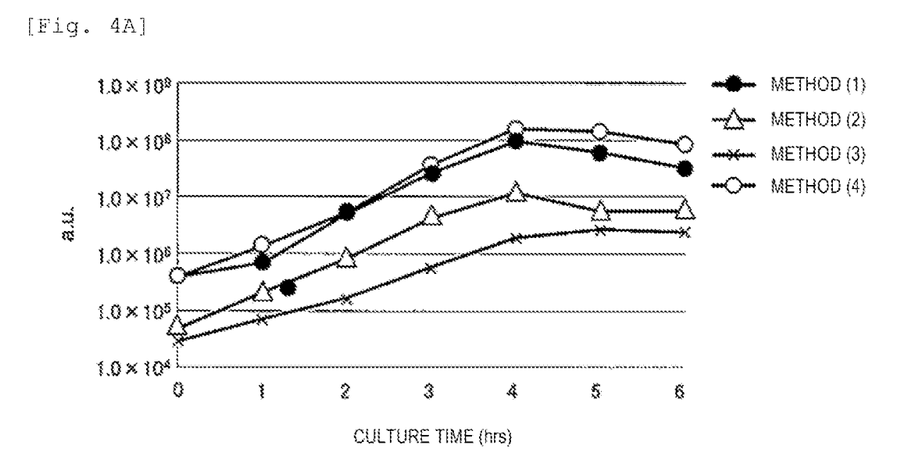
FIG. 4a is a graph illustrating an example of a time-dependent change in a live bacteria ATP luminescence amount and a dead bacteria ATP luminescence amount in the absence of antibiotics.
Figure 4B:
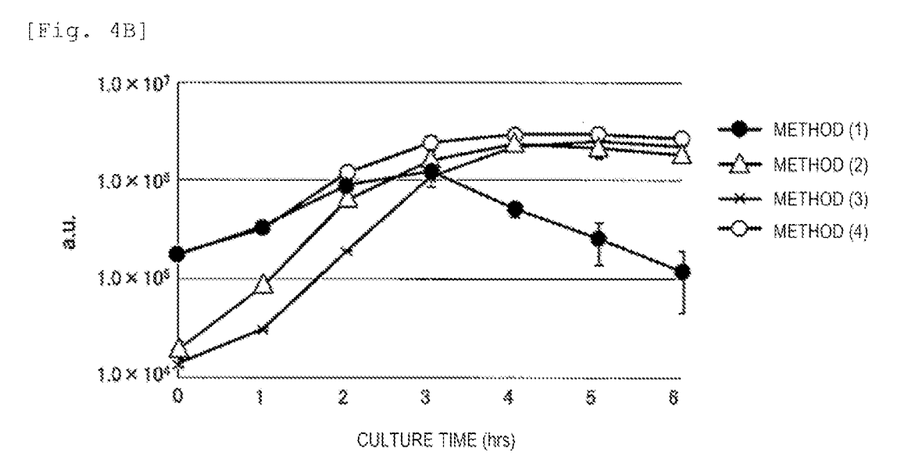
FIG. 4b is a graph illustrating an example of a time-dependent change in a live bacteria ATP luminescence amount and a dead bacteria ATP luminescence amount in the presence of antibiotics.

FIG. 4a illustrates a result obtained by culturing *E. coli* on the absence of antibiotics. FIG. 4b illustrates a result obtained by culturing *E. coli* in the presence of 8 μg/mL of ampicillin (hereinafter, referred to as ABPC) which is an antibiotic. If the results in FIGS. 4a and 4b are compared with each other, in FIG. 4a, according to the live bacteria ATP method in Method (1), the luminescence amount increases with the lapse of the culture time until four hours of the culture time. Thereafter, until five hours and six hours of the culture time, the luminescence amount tends to be saturated. In contrast, the submerged ATP method in Method (2) to the total ATP method in Method (4) also show the same tendency. On the other hand, in FIG. 4b, the luminescence amount of the live bacteria ATP according to Method (1) decreases with the lapse of the culture time (after three hours). In contrast, according to the submerged ATP method in Method (2) to the total ATP method in Method (4), the luminescence amount shows a tendency that the luminescence amount increases or does not vary greatly.

This shows a reaction in which during four hours of the culture time, ampicillin serving as the antibiotic acts on *E. coli*, and stops the growth of the live bacteria so as to kill the bacteria with the lapse of time. Since ATP derived from the dead bacteria leaks from the damaged site of the cell membrane as the cell membrane is progressively damaged, ATP in the bacteria culture liquid increases. The reason that the luminescence amount is constant in the liquid according to Method (2), in the filtrate according to Method (3), and in the total ATP according to Method (4) after four hours of the culture time is due to the result showing that any ATP derived from the dead bacteria increases.

Next, an example of a processing step performed by an antimicrobial susceptibility test system according to the present embodiment when the live bacteria ATP or the dead bacteria ATP is obtained will be described with reference to FIG. 5. As long as the bacteria serving as a measurement target of the test contains ATP inside the bacterial cell, a type of the bacteria is not particularly limited.

The specimen such as blood, pharyngeal swab, and sputum is collected from an infectious patient (S501), isolation culture is carried out for approximately 24 hours all day and night in order to obtain the infectious disease-causing bacteria as a single colony from the specimen in which indigenous bacteria coexist (S502). After the isolation culture, the bacteria forming the single colony are prepared to have a constant concentration (S503), the bacteria are distributed to a container in which various types and various concentrations of antimicrobials/antibiotics are arranged (S504), and antimicrobial susceptibility culture is carried out (S505).

Here, a material and a shape of the distribution container used in S505 are not particularly limited. However, it is desirable to use those which have a plate shape having a plurality of holes (wells) on a flat surface. A 96 well microplate in which 96 wells (8 wells×12 wells) in total are integrated with each other is used. Alternatively, a 384 well microplate in which 384 wells (16 wells×24 wells) in total are integrated with each other, or a 1,532 well microplate in which 1,532 wells (32 wells×48 wells) in total are integrated with each other is used.

In addition, the antimicrobials/antibiotics used for the antimicrobial susceptibility culture are not particularly limited. However, it is desirable to use the antibiotics having a bactericidal action, such as penicillin derivatives, cephem derivatives, aminoglycoside derivatives, new quinolone derivatives, and fosfomycin derivatives.

After the antimicrobial susceptibility culture is carried out for several hours, the live bacteria ATP derived from the live bacteria contained in the culture liquid is measured in accordance with a live bacteria ATP measurement flow. In addition, the dead bacteria ATP derived from the dead bacteria contained in the culture liquid is measured in accordance with a dead bacteria ATP measurement flow. Based on the measurement results of these measurement flows, the antimicrobial susceptibility of the bacteria is determined.

The live bacteria ATP measurement flow is configured to include an ATP eliminating step S506, an ATP extracting step S507, and luminescence measurement S508. In the ATP eliminating step S506, the free ATP outside the bacterial cell is removed. Without being particularly limited, a method of removing the free ATP includes a method of using ATP-degrading enzyme such as apyrase, or a method of removing the free ATP by means of filtering. In the ATP extracting step S507, the membrane of the bacterial cell is crushed, and ATP is extracted out from the membrane. Without being particularly limited, a method of crushing the membrane of the bacterial cell includes a method of crushing the membrane by adding a surfactant thereto, an ultrasonic irradiation method, or a method of crushing the membrane by using a French press or a homogenizer. Thereafter, the luminescence measurement S508 is performed.

The dead bacteria ATP measurement flow is configured to include a filtering step S509, a filtrate collecting step S510, and luminescence measurement S511. In the filtering step S509, the bacterial cell whose size is larger than the filter pore size is removed. In the filtrate collecting step S510, the filtrate is collected, and the luminescence measurement is performed (S511), thereby determining the amount of the dead bacteria ATP.

Figure 5:
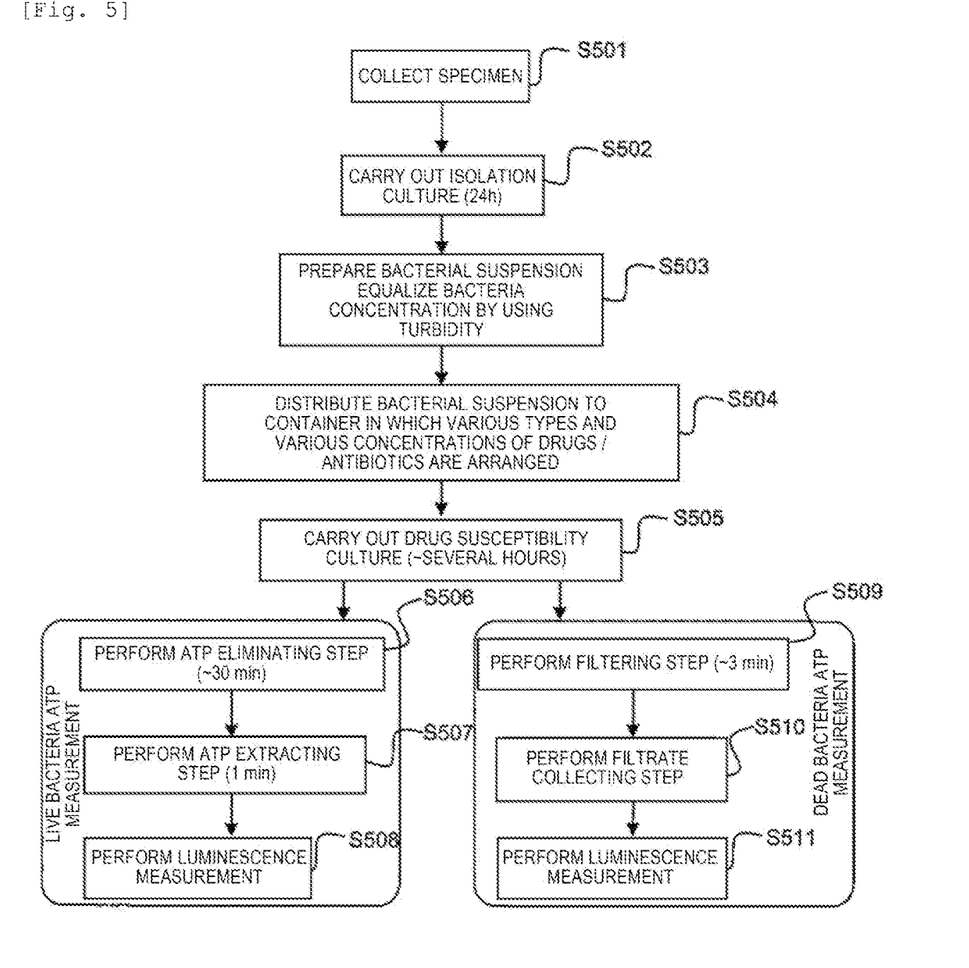
FIG. 5 is a flowchart illustrating an example of a processing step performed by an antimicrobial susceptibility test system.

In this way, in the dead bacteria ATP measurement flow illustrated in FIG. 5, ATP in the filtrate according to Method (3), that is, the free ATP5 leaking from the damage of the cell membrane is determined as the dead bacteria ATP. However, the measurement method of the dead bacteria ATP is not limited thereto, and may include a method of measuring the free ATP5 leaking from the bacterial cell in the culture liquid by using the culture liquid according to method (2) in FIG. 2 without any change. The total ATP (FIG. 2(4)) in the bacteria culture liquid may be a measurement target. In a case where the total ATP are the targets of the dead bacteria ATP measurement, a difference between the luminescence measurement S511 and the luminescence measurement S508 is regarded as the dead bacteria ATP. In a case of using Method (4), the measurement method includes a method of extracting ATP by adding a surfactant to the culture liquid, an ultrasonic irradiation method, or a method of extracting ATP from the bacterial cell by using a French press or a homogenizer.

Figure 7:
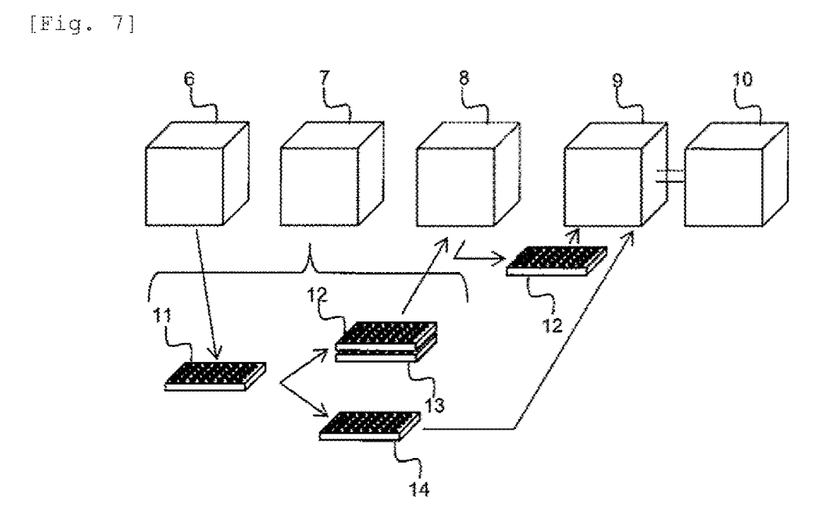
FIG. 7 is a view illustrating a configuration example of the antimicrobial susceptibility test system according to the present embodiment.

Next, a configuration example of the antimicrobial susceptibility test system according to the present embodiment will be described with reference to FIG. 7. This system is configured to include a culture vessel 6, a dispenser 7, a centrifuge 8, a measurement device 9, and a dead bacteria/live bacteria comparison unit 10. In the culture vessel 6, the culture of the bacterial cell serving as the target of the antimicrobial susceptibility test is carried out. After the bacterial cell culture, the dispenser 7 dispenses the bacterial cell liquid to each container of an antimicrobial susceptibility test plate 11. The dispenser 7 is equipped with a dispensing mechanism which can dispense the liquid of several microliters to several hundred microliters. The amount can be optionally changed in a range from 10 microliters to 200 microliters, but it is preferable to dispense the liquid of 100 microliters.

Next, a sample inside each container in the antimicrobial susceptibility test plate 11 in which the antimicrobial susceptibility test is completely carried out is dispensed to the container 12 having a filter in a bottom portion, and to a second luminescence measurement container 14. The dispenser 7 is equipped with the dispensing mechanism which can dispense the liquid of several microliters to several hundred microliters, and dispenses a predetermined sample amount to the container 12 having the filter in the bottom portion, and to the second luminescence measurement container 14. Then, the second luminescence measurement container 14 in which the dispensing step is completed by the dispenser 7 is introduced to the measurement device 9. In the centrifuge 8, in the preparation step of the dead bacteria ATP, filtering is performed in order to remove the bacterial cell from the bacteria culture liquid 1. The filtering container 12 having the filter in the bottom portion is installed in an upper portion of a first luminescence measurement container 13, and is subjected to centrifugation by the centrifuge 8. In this manner, the solution in the container 12 having the filter in the bottom portion is filtered, the filtrate is obtained in the first luminescence measurement container 13. Then, the first luminescence measurement container 13 is introduced to the measurement device 9.

The measurement device 9 performs ATP adjustment steps S506 and S507, and performs luminescence measurements S508 and S511 on the dead bacteria ATP. The dead bacteria/live bacteria comparison unit 10 calculates a live bacteria ATP luminescence amount and a dead bacteria ATP luminescence amount from the ATP luminescence amount measured by the measurement device 9, and determines a ratio of the dead bacteria ATP luminescence amount/the live bacteria ATP luminescence amount. After the bacteria forming the single colony are prepared to have a constant concentration (S503), the dispenser 7 can also be used for a step (S504) of distributing the bacteria to the container in which various types and various concentrations of antimicrobials/antibiotics are arranged.

Figure 9:
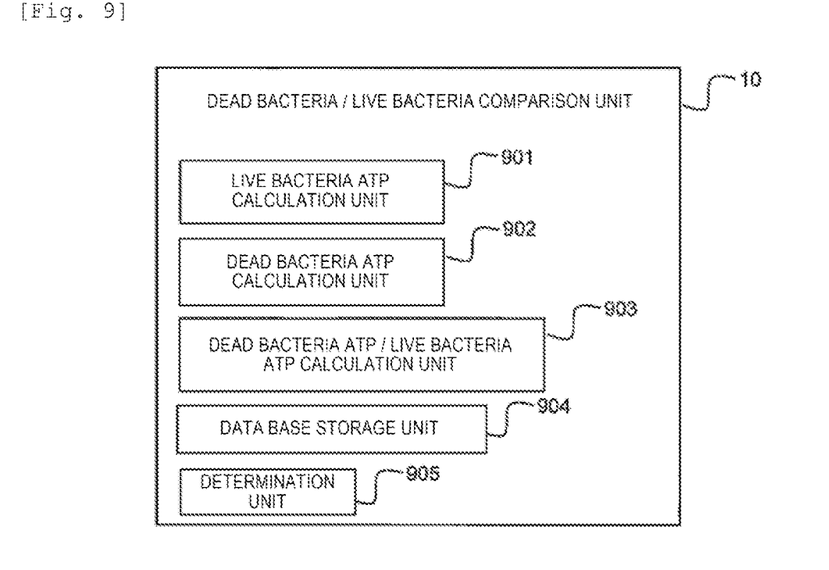
FIG. 9 is a block diagram illustrating an internal configuration of a dead bacteria/live bacteria comparison unit.

FIG. 9 illustrates a functional block configuration diagram of the dead bacteria/live bacteria comparison unit 10. The dead bacteria/live bacteria comparison unit 10 is configured to include a live bacteria ATP calculation unit 901, a dead bacteria ATP calculation unit 902, a dead bacteria ATP/live bacteria ATP calculation unit 903 which displays a result by summarizing the processes in the units 901 and 902 as a final result, a database storage unit 904, and a determination unit 905.

Specifically, the result of the luminescence measurement (S508) in FIG. 5 is stored in the live bacteria ATP calculation unit 901, and the result of the luminescence measurement (S511) is stored in the dead bacteria ATP calculation unit 902. If the dead bacteria ATP luminescence amount is set to x and the live bacteria ATP luminescence amount is set to y, the dead bacteria ATP/live bacteria ATP calculation unit 903 stores the dead bacteria ATP luminescence amount/the live bacteria ATP luminescence amount as a value of x/y, and displays the value as the final result of the amount ratio of the dead bacteria ATP amount/the live bacteria ATP amount. As a matter of course, both of these can also be separately displayed, and only the results in S508 and S511 can also be displayed.

In addition, the database storage unit 904 stores a determination standard which is created as a database for each type of the bacteria based on the calculation result of the luminescence amount ratio (x/y) calculated in the past by the dead bacteria ATP/live bacteria ATP calculation unit 903. Based on the determination standard, the determination unit 905 determines the presence or absence of the antimicrobial susceptibility. For example, when the type of the bacteria is identified, the determination unit 905 selects the type of the bacteria from the database storage unit 904, reads a threshold of the ratio (x/y) of the live bacteria ATP luminescence amount (S508)/the dead bacteria ATP luminescence amount (S511) which serves as the determination standard, and compares the calculation result obtained by the dead bacteria ATP/live bacteria ATP calculation unit 903 with the threshold, thereby determining the presence or absence of the antimicrobial susceptibility. In this manner, accurate determination based on the test result in the past can be made. However, the determination standard stored in the database storage unit 904 may not necessarily based on the calculation result obtained in the past by the dead bacteria ATP/live bacteria ATP calculation unit 903. A configuration may be adopted in which a predetermined threshold is set in advance.

Figure 10:
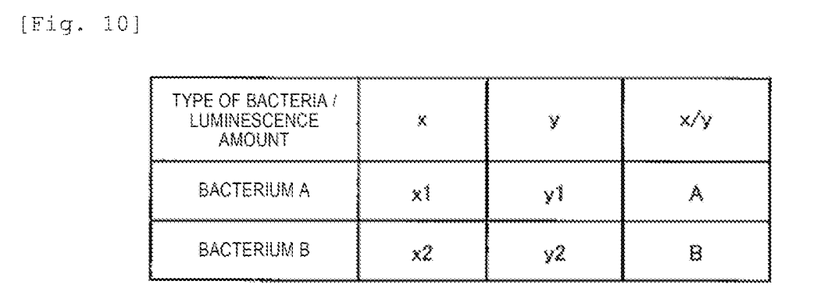
FIG. 10 is a table illustrating an example of a database serving as a determination standard of the antimicrobial susceptibility test.

FIG. 10 illustrates an example of the determination standard to be stored in the database storage unit 904. For each type of the bacteria, the database storage unit 904 stores the dead bacteria luminescence amount (x), the live bacteria luminescence amount (y), and the dead bacteria ATP luminescence amount/the live bacteria ATP luminescence amount (x/y) indicating the amount ratio between the dead bacteria ATP and the live bacteria ATP. In a case of a bacterium A as an example, if the dead bacteria ATP luminescence amount/the live bacteria ATP luminescence amount (x/y) calculated based on the dead bacteria luminescence amount (x) and the live bacteria luminescence amount (y) of the bacterial solution measured after the culture is carried out for a certain period of time is greater than A, the determination unit 905 determines that the bacterium A has susceptibility to the antimicrobial. Conversely, in a case where the dead bacteria ATP luminescence amount/the live bacteria ATP luminescence amount (x/y) is equal to or smaller than A, the determination unit 905 determines that the bacterium A does not have the susceptibility to the antimicrobial, that is, the bacterium A is antimicrobial-resistant.

Figure 8:
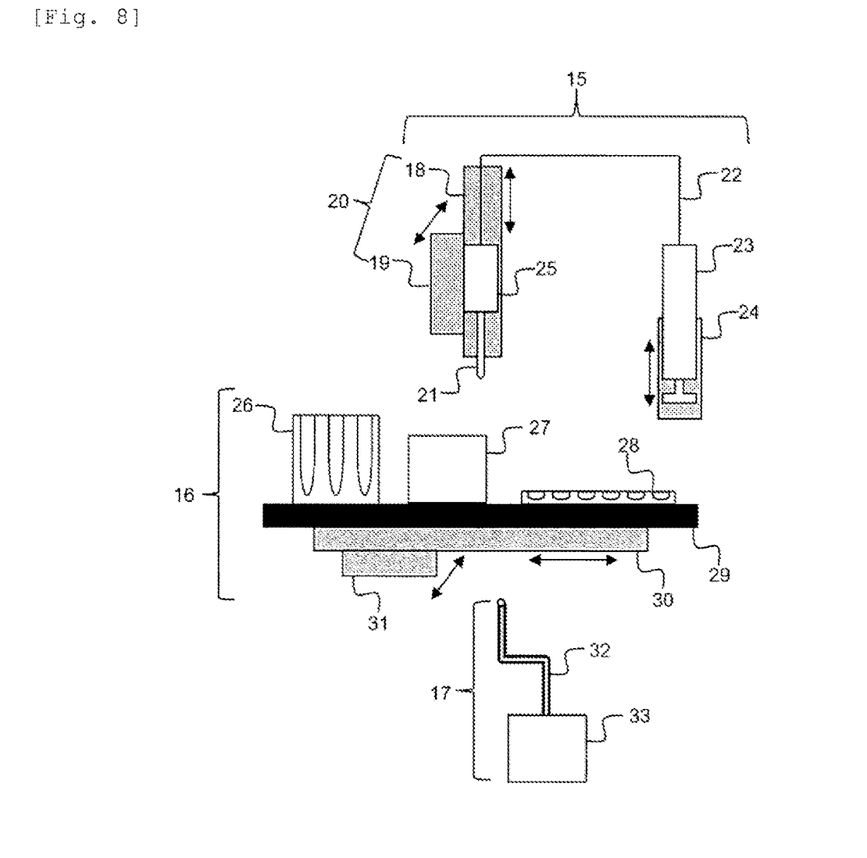
FIG. 8 is a view illustrating an internal configuration of a measurement device.

FIG. 8 illustrates an example of an internal configuration of the measurement device 9. The measurement device 9 is configured to include a reagent dispensing mechanism 15, a sample preparation mechanism 16, and a luminescence detection mechanism 17.

The reagent dispensing mechanism 15 is configured to include a first electric actuator 18, a position adjustment mechanism 20 using a second electric actuator 19, a dispensing nozzle 21, a tube pipe 22, a syringe 23, and further a third electric actuator 24 for actuating the syringe 23. The dispensing nozzle 21 and the tube pipe 22 are linked to each other by using a fixing portion 25.

The reagent is loaded and unloaded by causing a piston of the syringe 23 to vertically move in conjunction with the vertical movement of the third electric actuator 24 used for pushing and pulling the syringe 23. The reagent inside a reagent folder 26 can be collected or can be dispensed to a luminescence measurement container 28. In addition, the position adjustment mechanism 20 can move the dispensing nozzle 21 to each suitable position on the reagent folder 26 and the luminescence measurement container 28.

The sample preparation mechanism 16 is configured to include a stage 29 for installing the reagent folder 26 and the luminescence measurement container 28, a first electric slider 30, and a second electric slider 31 which can move the stage to any optional position. The reagent folder 26 contains an eliminating reagent and an extracting reagent which are used in live bacteria ATP preparation steps S506 and S507, and a luminescence reagent used in ATP luminescence measurement steps S508 and S511. In addition to these reagents, appropriately required reagents can be loaded on the reagent folder 26. For example, a first cleaning solution for cleaning the nozzle in order to prevent cross contamination, a second cleaning solution for cleaning all of the dispensing nozzle 21 coming into contact with the reagent of the dispensing mechanism, the tube pipe 22, and the inside of the syringe 23, and an empty container for storing the first cleaning solution and the second cleaning solution after cleaning can also be loaded on the reagent folder 26.

In order to prevent the above-described cross contamination, a case is also conceivable where the dispensing nozzle 21 is exchanged for every measurement. In this regard, a chip group installation unit 27 for installing a disposable chip is arranged on the stage 29 of the measurement device 9 of the antimicrobial susceptibility testing system according to the present invention. The dispensing nozzle 21 is accessible to the chip group installation unit 27 by the position adjustment mechanism 20, thereby automatically attaching and detaching the chip.

The bottom portion of the stage 29 at the installation place of the luminescence measurement container 28 is transparent or a member thereof is cut out, thereby enabling the luminescence detection mechanism 17 to detect the luminescence. The first electric slider 30 of the stage 29, the second electric slider 31, and the position adjustment mechanism 20 of the reagent dispensing mechanism 15 perform position control in conjunction with each other, thereby dispensing the reagent to any optional target container (well) on the luminescence measurement container 28 from the dispensing nozzle 21.

The method of detecting the luminescence in the luminescence detection mechanism 17 is not particularly limited. However, according to the present embodiment, FIG. 8 illustrates an example of using a photomultiplier tube (hereinafter, referred to as a PMT). The luminescence detection mechanism 17 is configured to include an optical fiber cable 32 and a PMT 33. The optical fiber cable 32 and the PMT 33 are connected to each other by a fiber coupler, thereby transmitting light incident on a distal end of the optical fiber to a light receiving element of the PMT 33. This form of the luminescence measurement container 28 employs those in which the distal end diameter of the optical fiber cable 32 is approximately the same as or smaller than that of each container of the luminescence measurement container 28. Accordingly, it is possible to detect the luminescence at a specific position on the luminescence measurement container 28. In addition, the first electric slider 30 and the second electric slider 31 enable the luminescence to be measured in any target container (well) on the luminescence measurement container 28. In terms of sensitivity, PMT is preferably used. However, as a detector, not only the PMT 33 but also a CCD camera or a photodiode are replaceable.

Hitherto, the configuration example of the antimicrobial susceptibility test system has been described with reference to FIGS. 7, 8, and 9. Here, FIG. 7 illustrates the device which is divided into the culture vessel 6, the dispenser 7, the centrifuge 8, the measurement device 9, and the dead bacteria/live bacteria comparison unit 10 for each function. However, as a matter of course, a fully automatic system in which all of these are integrated with each other may be employed. In this case, at proper timing, the antimicrobial susceptibility test plate 11, the container 12 having the filter in the bottom portion, the first luminescence measurement container 13, and the second luminescence measurement container 14 are moved to the culture vessel 6, the dispenser 7, the centrifuge 8, and the measurement device 9, and a loadable robot arm is prepared. In this manner, a system configured to have a form which can continuously perform the processes may be employed.

In addition, each functional block described in FIG. 9 may be realized by an installed software module or hardware. That is, each functional block can be realized by software which causes a processor to interpret and execute a program stored in a memory for realizing each function in the dead bacteria/live bacteria comparison unit 10. In addition, for example, each functional block may be realized by hardware in such away that the respective functional blocks are partially or entirely designed using an integrated circuit. For example, information such as programs for realizing each function, files, databases, function data, and viable data can be stored in a recording device such as a memory, a hard disk, and a solid state drive (SSD) or a recording medium such as an IC card, an SD card, and a DVD.

Figure 6:
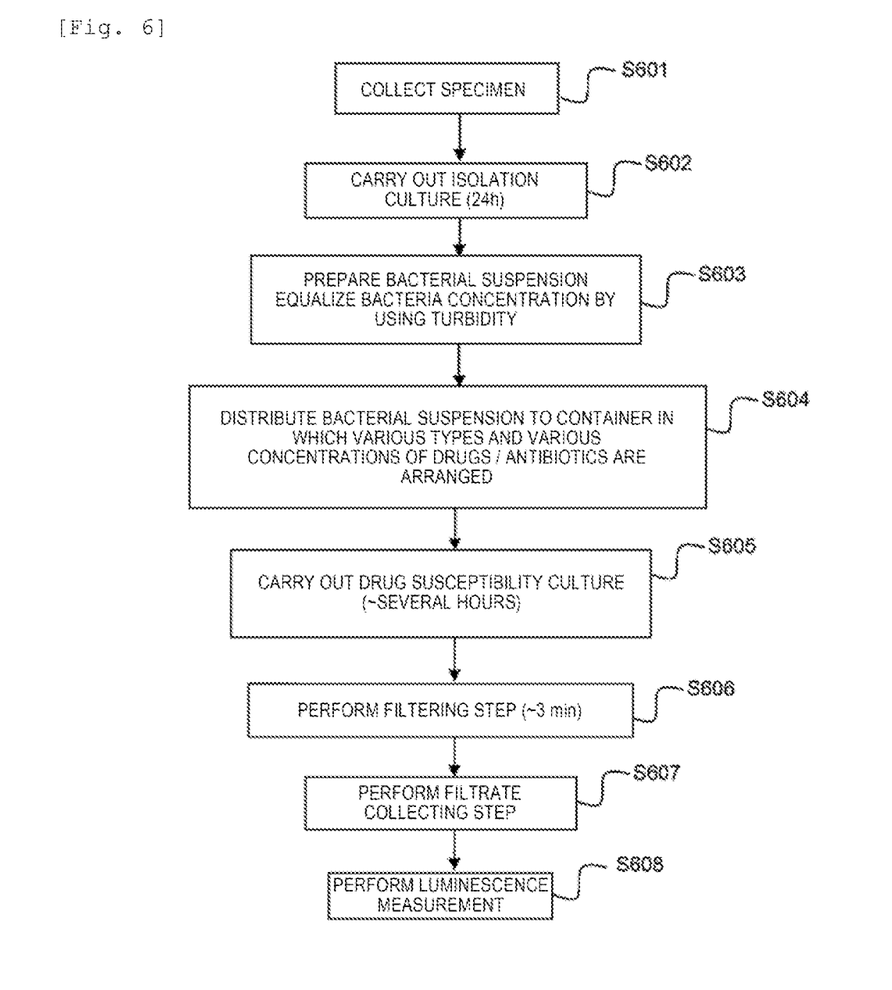
FIG. 6 is a flowchart illustrating an example of a measurement step of the dead bacteria ATP luminescence amount measured by the antimicrobial susceptibility test system.

Furthermore, as the determination standard of the antimicrobial susceptibility determined by the determination unit 905, in addition to the method of using both the measurement results of the live bacteria ATP luminescence amount and the dead bacteria ATP luminescence amount which are illustrated in FIG. 5, only the measurement result of the dead bacteria ATP luminescence amount illustrated in FIG. 6 can also be used. The luminescence amount measurement in this case complies with the method of measuring the dead bacteria ATP amount illustrated in FIG. 5. Specifically, in S601 to S605 in FIG. 6, operations the same as those in S501 to S505 in FIG. 5 are performed. In S606 to S608 in FIG. 6, operations the same as those in S509 to S511 in FIG. 5 are performed.

Hereinafter, a determination example of the antimicrobial susceptibility according to the present embodiment will be described in detail with reference to content of experiments.

In this experiment, *Escherichia coli* (ATCC25922 strain; hereinafter, referred to as *E. coli*) and *Staphylococcus aureus* (ATCC25923; hereinafter, referred to as *S. aureus*) are used as the bacterial cell. An antimicrobial susceptibility test using the ATP method is carried out for both of these. As antibiotics, ampicillin and levofloxacin (hereinafter, referred to as LVFX) are used.

First, the bacterial cells are cultured overnight on an LB agar medium, and the next day, a colony is suspended in a Mueller-Hinton (hereinafter, referred to as MH) medium, thereby preparing a bacterial suspension prepared in 0.5 McFarland. Next, the bacterial suspension diluted 500 times in the MH medium is distributed as much as each 50 μL to the plate to which the MH medium containing the antibiotic whose concentration is twice the final concentration is distributed in advance as much as each 50 μL. The static culture is carried out at 37° C. for a certain period of time, and the bacterial suspension is prepared. For the final concentration of the antibiotic, ABPC is set to 4 μg/mL and LVFX is set to 0.125 μg/mL in a case where *E. coli* is a measurement target. In a case where *S. aureus* is a measurement target, ABPC is set to 0.25 μg/mL and LVFX is set to 0.125 μg/mL. The bacterial cells are compared with the bacterial cells cultured in the MH medium having no antibiotic contained therein.

The live bacteria ATP is prepared by mixing 2 μL of the ATP eliminating solution with 18 μL of the above-described bacteria culture liquid, and the mixture is left static at room temperature for 30 minutes. Thereafter, 20 μL of the ATP extracting reagent is mixed therewith, and the mixture is left static at room temperature for one minute so as to prepare the live bacteria ATP. The dead bacteria ATP is prepared by adding the bacteria culture liquid onto a filter (membrane pore size 0.22 μm). The filtrate obtained through filtering using centrifugation is used as the dead bacteria ATP. The luminescence reagent is added to the prepared live bacteria ATP or dead bacteria ATP, and is subjected to photon counting for one minute. The obtained luminescence amount (amount of luminescence (a.u.)) is used as an index of the ATP amount.

Figure 11:
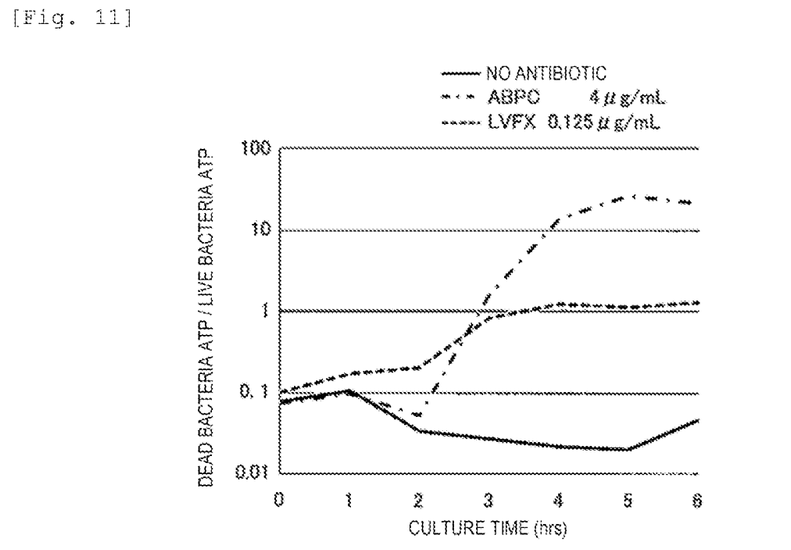
FIG. 11 is a graph illustrating an example of an ATP amount ratio with the lapse of a culture time of *E. coli*.
Figure 12:
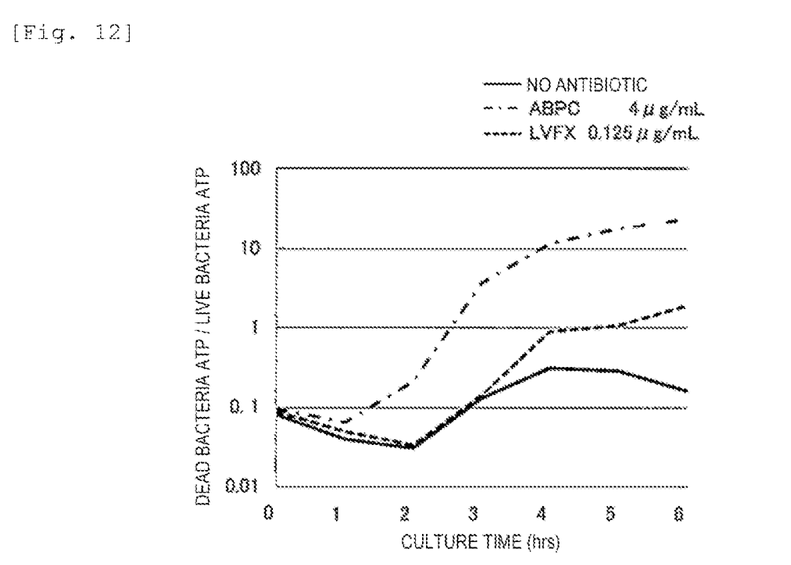
FIG. 12 is a graph illustrating an example of an ATP amount ratio with the lapse of a culture time of *S. aureus*.

According to the above-described experiment, a luminescence amount ratio between the dead ATP luminescence amount and the live ATP luminescence amount is obtained. FIGS. 11 and 12 illustrate a result obtained by calculating the luminescence amount ratio as an amount ratio between the live bacteria ATP and the dead bacteria ATP.

FIG. 11 illustrates the amount ratio between the live bacteria ATP and the dead bacteria ATP of *E. coli*. In the medium having no antibiotic contained therein, the ratio of the dead bacteria ATP luminescence amount/the live bacteria ATP luminescence amount, that is, the ratio of the dead bacteria ATP amount/the live bacteria ATP amount is changed to approximately 0.1 or smaller. On the other hand, in the presence of ABPC or LVFX, as the culture time elapses, the ratio of the dead bacteria ATP amount/the live bacteria ATP amount increases. If the standard to determine an effect of the antibiotic is set to the ratio of the dead bacteria ATP amount/the live bacteria ATP amount=1, the result shows that the effect of ABPC and LVFX with respect to *E. coli* can be determined in approximately three hours after the antimicrobial susceptibility culture starts.

Next, FIG. 12 illustrates the amount ratio between the live bacteria and the dead bacteria of *S. aureus*. In the medium having no antibiotic contained therein, the ratio of the dead bacteria ATP amount/the live bacteria ATP amount is changed to approximately 0.5 or smaller. In the presence of ABPC or LVFX, similarly to the case of *E. coli*, as the culture time elapses, the ratio of the dead bacteria ATP amount/the live bacteria ATP amount increases. If the standard to determine an effect of the antibiotic is set to the ratio of the dead bacteria ATP amount/the live bacteria ATP amount=1, the result shows that the effect of ABPC with respect to *S. aureus* can be determined in approximately two and a half hours, and the effect of LVFX with respect to *S. aureus* can be determined in approximately four hours after the antimicrobial susceptibility culture starts.

Through the above-described experiments, as the determination standard of the antimicrobial susceptibility test using the ATP method, the live bacteria ATP amount and the dead bacteria ATP amount in the reaction system containing the antimicrobial are obtained based on the ATP luminescence amount, and the ATP amount ratio between the live bacteria and the dead bacteria is used. In this manner, it is possible to determine the antimicrobial susceptibility by using the same determination standard for different types of the bacteria. Therefore, it is apparent that the effect of the antimicrobial can be more quickly and accurately determined compared to the related art.

In other words, according to the antimicrobial susceptibility test system in the present embodiment, it is possible to shorten the time required for the antimicrobial susceptibility culture in the antimicrobial susceptibility test of the bacteria, which employs the ATP method. It is found that the effect of the antimicrobial can be determined through measurements which are less frequently performed. In this manner, the antimicrobial susceptibility test is quickly and easily performed, thereby enabling the antibiotics to be immediately and properly administered to a seriously infectious patient.

Furthermore, according to the antimicrobial susceptibility test system in the present embodiment, the live bacteria ATP amount is obtained from the ATP amount included in the membrane of the bacteria, and the dead bacteria ATP amount is obtained from the free ATP amount included in the reaction system. In this manner, unlike the technique of determining the number of live bacteria/the number of dead bacteria in the related art, both the live bacteria and the dead bacteria can be counted using the ATP method. Thus, there is no possibility that a counting error may occur due to a method difference. Accordingly, the number of live bacteria and the number of dead bacteria can be very accurately counted. In addition, since the counting method is used with the ATP method in a unified manner, it is possible to realize a simple device configuration.

REFERENCE SIGNS LIST

1 BACTERIA CULTURE LIQUID,
2 LIVE BACTERIUM,
3 DEAD BACTERIUM,
4 DEAD BACTERIUM,
5 ATP,
6 CULTURE VESSEL,
7 DISPENSER,
8 CENTRIFUGE,
9 MEASUREMENT DEVICE,
10 DEAD BACTERIA/LIVE BACTERIA COMPARISON UNIT,
11 ANTIMICROBIAL SUSCEPTIBILITY TEST PLATE,
12 FILTERING CONTAINER,
13 FIRST LUMINESCENCE MEASUREMENT CONTAINER,
14 SECOND LUMINESCENCE MEASUREMENT CONTAINER,
15 REAGENT DISPENSING MECHANISM,
16 SAMPLE PREPARATION MECHANISM,
17 LUMINESCENCE DETECTION MECHANISM,
18 FIRST ELECTRIC ACTUATOR,
19 SECOND ELECTRIC ACTUATOR,
20 POSITION ADJUSTMENT MECHANISM,
21 DISPENSING NOZZLE,
22 TUBE PIPE,
23 SYRINGE,
24 THIRD ELECTRIC ACTUATOR,
25 FIXING PORTION,
26 REAGENT FOLDER,
27 CHIP GROUP INSTALLATION UNIT,
28 LUMINESCENCE MEASUREMENT CONTAINER,
29 STAGE,
30 FIRST ELECTRIC SLIDER,
31 SECOND ELECTRIC SLIDER,
32 OPTICAL FIBER,
33 PMT

The invention claimed is:

1. An antimicrobial susceptibility test system comprising:
a culture vessel that cultures a bacterial cell in a culture liquid;
a dispenser that dispenses an antimicrobial into a distribution container to which the culture liquid containing the bacterial cell is distributed and dispenses the culture liquid from the distribution container to a filtering container disposed above a first luminescence measurement container and to a second luminescence measurement container, the filtering container having a filter in a bottom portion;
wherein the filter filters the culture liquid in the filtering container and obtains a filtrate into the first luminescence measurement container; and
a test device that has a luminescence detector and a determination unit, the luminescence detector measuring ATP luminescence of the filtrate in the first luminescence measurement container and the culture liquid in the second luminescence measurement container, and the determination unit being programmed to determine the presence or absence of antimicrobial susceptibility of the bacteria, based on an ATP luminescence amount derived from dead bacteria in the culture liquid,
wherein the luminescence detector measures an ATP luminescence amount derived from live bacteria in the culture liquid in the second luminescence measurement container and the ATP luminescence amount derived from the dead bacteria in the filtrate in the first luminescence measurement container, and
wherein the determination unit is programmed to determine the presence or absence of antimicrobial susceptibility of the bacteria, based on a luminescence amount ratio between the ATP luminescence amount derived from the live bacteria and the ATP luminescence amount derived from the dead bacteria.

2. The antimicrobial susceptibility test system according to claim 1, wherein the determination unit is programmed to perform the determination by regarding a luminescence amount of free ATP included in the filtrate as the ATP luminescence amount derived from the dead bacteria.

3. The antimicrobial susceptibility test system according to claim 1, further comprising:
a database storage that stores a threshold for the determination,
wherein the determination unit is programmed to refer to the threshold and determine the presence or absence of antimicrobial susceptibility of the bacteria, based on a comparison result of a luminescence amount ratio between the ATP luminescence amount derived from the live bacteria and the ATP luminescence amount derived from the dead bacteria and the threshold.

4. The antimicrobial susceptibility test system according to claim 3,
wherein the determination unit is programmed to refer to the threshold, and determine that the antimicrobial susceptibility of the bacteria is present in a case where the luminescence amount ratio is greater than the threshold.

5. The antimicrobial susceptibility test system according to claim 3,
wherein the database storage stores the threshold, based on the luminescence amount ratio obtained by the determination in the past.

6. The antimicrobial susceptibility test system according to claim 3,
wherein the determination unit is programmed to set the ATP luminescence amount derived from the dead bacteria to x and the ATP luminescence amount derived from the live bacteria to y, calculate a value of x/y, and determine the presence or absence of antimicrobial susceptibility of the bacteria by referring to a value of x/y for each type of the bacteria calculated in a past and stored in the database storage.

7. The antimicrobial susceptibility test system according to claim 1,
wherein the luminescence detector performs the measurement at constant incubation time intervals.

8. The antimicrobial susceptibility test system according to claim 1,
wherein the filter performs the filtration by a centrifuge.

9. The antimicrobial susceptibility test system according to claim 1,
wherein the distribution container is a micro well plate to which a plurality of types of the antimicrobial is distributed.

10. The antimicrobial susceptibility test system according to claim 1,
wherein the distribution container is a micro well plate to which a plurality of concentrations of the antimicrobial is distributed.

11. An antimicrobial susceptibility test system comprising:
a culture vessel to culture a bacterial cell in a culture liquid;
a dispenser to dispense an antimicrobial into a distribution container to which the culture liquid containing the bacterial cell is distributed and dispense the culture liquid from the distribution container to a filtering container disposed above a first luminescence measurement container and to a second luminescence measurement container, the filtering container having a filter in a bottom portion to filter the culture liquid in the filtering container and obtain a filtrate into the first luminescence measurement container; and
a test device that has a luminescence detector and a determination unit, the luminescence detector measuring ATP luminescence of the filtrate in the first luminescence measurement container and the culture liquid in the second luminescence measurement container, the determination unit determining the presence or absence of antimicrobial susceptibility of the bacteria based on an ATP luminescence amount derived from dead bacteria in the culture liquid;
wherein the luminescence detector is configured to measure an ATP luminescence amount derived from live bacteria in the culture liquid in the second luminescence measurement container and the ATP luminescence amount derived from the dead bacteria in the filtrate in the first luminescence measurement container; and
wherein the determination unit is programmed to determine the presence or absence of antimicrobial susceptibility of the bacteria, based on a luminescence amount ratio between the ATP luminescence amount derived from the live bacteria and the ATP luminescence amount derived from the dead bacteria in the culture liquid.

12. The antimicrobial susceptibility test system according to claim 11,
wherein the determination unit is programmed to perform the determination by regarding a luminescence amount of free ATP included in the filtrate as the ATP luminescence amount derived from the dead bacteria.

13. The antimicrobial susceptibility test system according to claim 11, further comprising:
a computer memory that stores a threshold for the determination,
wherein the determination unit is programmed to refer to the threshold and determine the presence or absence of antimicrobial susceptibility of the bacteria, based on a comparison result of a luminescence amount ratio between the ATP luminescence amount derived from the live bacteria and the ATP luminescence amount derived from the dead bacteria and the threshold.

14. The antimicrobial susceptibility test system according to claim 13,
wherein the determination unit is programmed to refer to the threshold, and determine that the antimicrobial susceptibility of the bacteria is present in a case where the luminescence amount ratio is greater than the threshold.

15. The antimicrobial susceptibility test system according to claim 13,
wherein the computer memory stores the threshold, based on the luminescence amount ratio obtained by the determination in the past.

16. The antimicrobial susceptibility test system according to claim 13,
wherein the determination unit is programmed to set the ATP luminescence amount derived from the dead bacteria to x and the ATP luminescence amount derived from the live bacteria to y, calculate a value of x/y, and determine the presence or absence of antimicrobial susceptibility of the bacteria by referring to a value of x/y for each type of the bacteria calculated in a past and stored in the computer memory.

17. The antimicrobial susceptibility test system according to claim 11, wherein the luminescence detector performs the measurement at constant incubation time intervals.

18. The antimicrobial susceptibility test system according to claim 11,
wherein the filter performs the filtration by a centrifuge.

19. The antimicrobial susceptibility test system according to claim 11,
wherein the distribution container is a micro well plate to which a plurality of types of the antimicrobial is distributed.

20. The antimicrobial susceptibility test system according to claim 11,
wherein the distribution container is a micro well plate to which a plurality of concentrations of the antimicrobial is distributed.

* * * * *